United States Patent [19]

Anderson et al.

[11] Patent Number: 5,030,223
[45] Date of Patent: Jul. 9, 1991

[54] HEAD MOUNTED STEREOTAXIC APPARATUS

[75] Inventors: Lloyd L. Anderson; Leon E. Girard, both of Ames, Iowa

[73] Assignee: Iowa State University Research Foundation, Inc., Ames, Iowa

[21] Appl. No.: 374,443

[22] Filed: Jun. 30, 1989

[51] Int. Cl.⁵ .................................................. A61B 19/00
[52] U.S. Cl. ...................................... 606/130; 128/630
[58] Field of Search ............... 606/130; 248/124, 285; 128/630

[56] References Cited

U.S. PATENT DOCUMENTS

| | | |
|---|---|---|
| 3,021,842 | 2/1962 | Flood . |
| 3,357,431 | 12/1967 | Newell .............................. 606/130 |
| 3,542,030 | 11/1970 | Hoffman et al. . |
| 3,817,249 | 6/1974 | Nicholson . |
| 4,230,117 | 10/1980 | Anichkov . |
| 4,256,112 | 3/1981 | Kopf et al. ......................... 606/130 |
| 4,341,220 | 7/1982 | Perry . |
| 4,592,352 | 6/1986 | Patil .................................... 606/130 |
| 4,841,967 | 6/1989 | Chang et al. ....................... 606/130 |

FOREIGN PATENT DOCUMENTS 3358997 11/1983 U.S.S.R. ............................... 606/130

Primary Examiner—Robert A. Hafer
Assistant Examiner—Kerry Owen
Attorney, Agent, or Firm—Henderson & Sturm

[57] ABSTRACT

A head mounted stainless steel stereotaxic apparatus for precise locallization of probes/cannulas in selected regions of the mammalian brain. Novel aspects of this apparatus include versatility in placement of probe/cannula in selected sites in the brain, mobility of the animal after attachment of the apparatus to the frontal bone, and repeated use of the same instrument on different animal species.

6 Claims, 3 Drawing Sheets

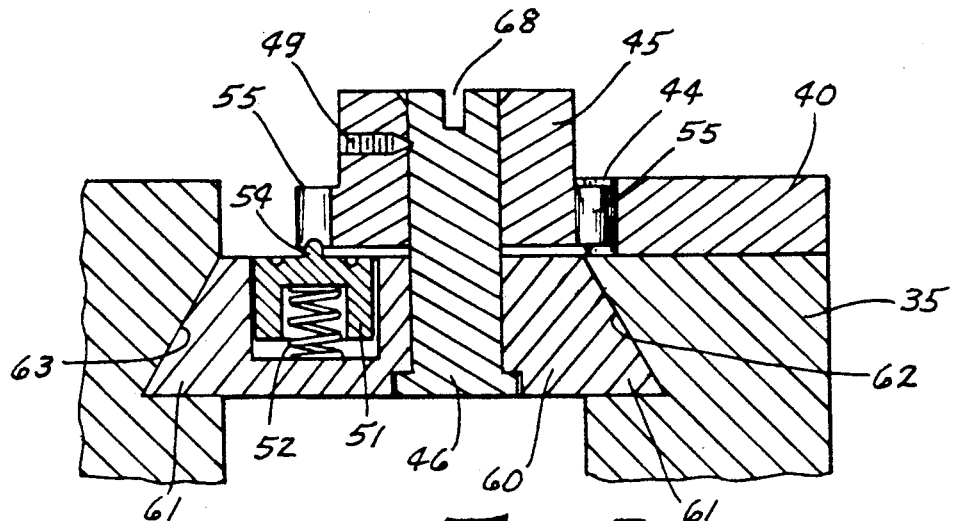
Fig. 7
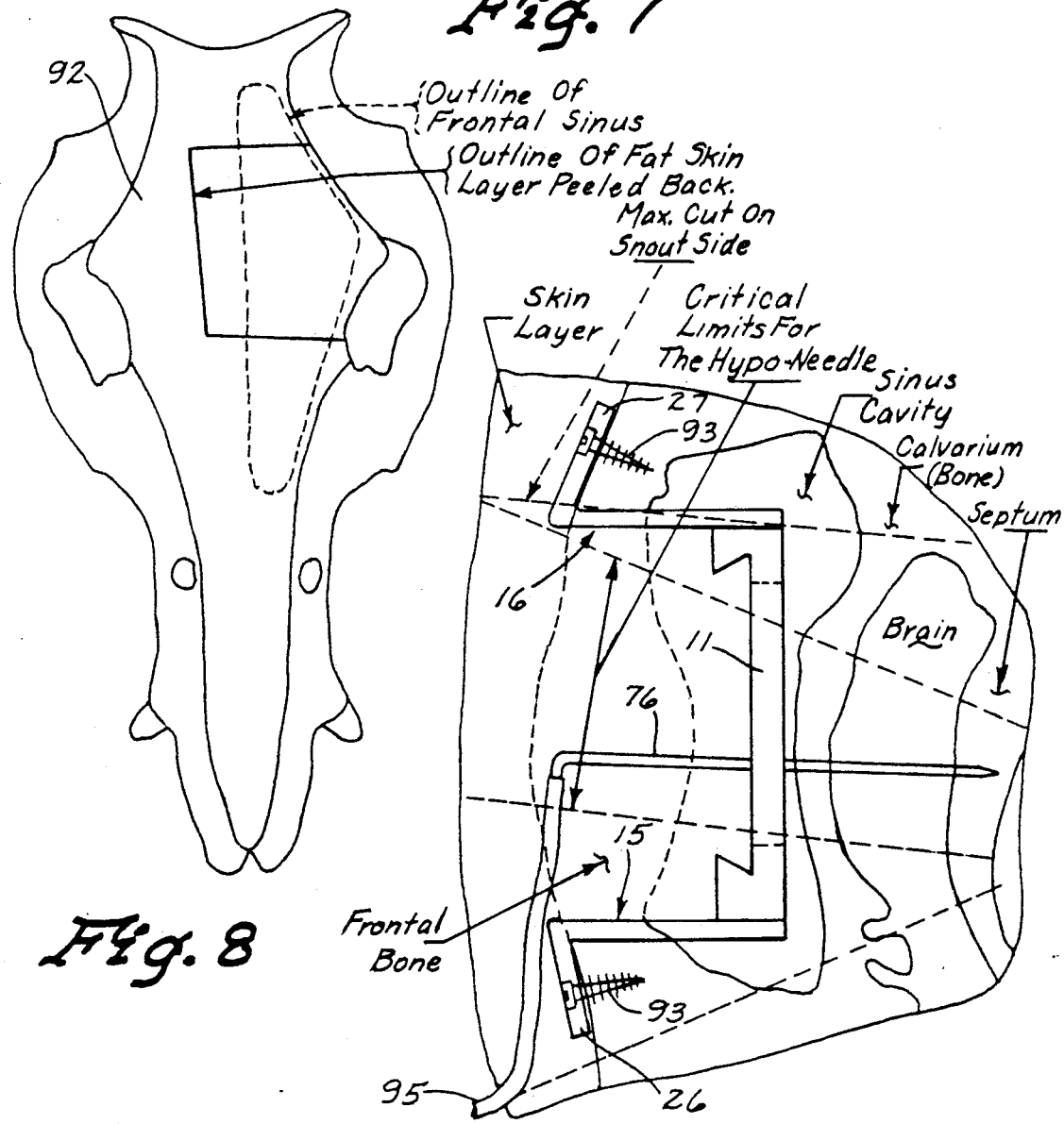
Fig. 8
Fig. 9

HEAD MOUNTED STEREOTAXIC APPARATUS

TECHNICAL FIELD

The present invention relates generally to a head mounted stereotaxic apparatus and more particularly to one which allows versatile adjustment in placement of probes or cannula in selected sites of the brain of an animal while still allowing mobility of the animal after attachment of the apparatus to the frontal bone.

BACKGROUND ART

Generally there is a need for devices to accurately position a probe onto an animal for infusing drugs or hormones into different ventricles, for removing fluids from ventricles to study the changes in hormones due to such removal, for probing the thalamus and hypothalamus by the use of electrical probes to stimulate parts of the brain, to record electrical brain activity, and for implanting crystalline steroids or peptide hormones into the brain by use of a probe through cannula.

Various types of devices have been devised for doing one or more of the above mentioned functions, such as U.S. Pat. Nos. 3,542,030 to Hoffman et al and 3,817,249 to Nicholson. In the Hoffman et al device, the animal must be restrained while the device is in use. This can be difficult to do and also causes the animal to be excited, which may affect the function of the brain that the scientist wishes to study. Furthermore, it may be necessary to drug the animal in order to use the device which also can affect the function of the brain to be studied.

In the Nicholson device, a removable grid plate is implanted in an animal's skull for positioning electrodes in an animal's brain. While this device is functional for positioning electrodes, there is a need for a head mounted stereotaxic apparatus which is more versatile and which does not have the disadvantages of the prior art referred to above.

DISCLOSURE OF THE INVENTION

The present invention relates to a head mounted stereotaxic apparatus including a brain probe and apparatus for positioning the brain probe precisely in selected sites of the brain of an animal while allowing mobility of the animal after attachment of the apparatus to the frontal bone of such animal.

A skin layer overlying the frontal sinus of the animal is peeled back to expose the frontal bone having the sinus cavity therebelow. The frontal bone is then removed and the sinus cavity is removed down to the calvarium bone. A base member is then attached to portions of the frontal bone which remain to position the base member just above the brain and adjacent to the calvarium bone.

A first translating member is slidably attached to the base member and has a locking mechanism thereon for locking the first translating member against movement with respect to the base member when it is in a desired position.

A second translating member has an opening therethrough and is slidably attached to the first translating member in a line transverse to the movement of the first translating member. Structure is provided for moving the second translating member back and forth with respect to the first translating member and for selectively locking the second translating member with respect to the first translating member. A tube extends through the opening in the second translating member and this tube is pivotally adjustable for permitting the tube to be universally pivoted 360° about a point. A locking mechanism is also provided for holding the tube at whatever pivotal position is desired. The position of the tube can be moved in or out with respect to the second translating member and can be locked at whatever distance into the skull that it extends.

An object of the present invention is to provide an improved head mounted stereotaxic apparatus.

A further object of the present invention is to provide a brain probe positioning apparatus which is versatile in placement of probe/cannula in selected sites of the brain of an animal.

A still further object of the present invention is to provide the versatile placement referred to above while still permitting mobility of the animal after attachment of such apparatus to the frontal bone of the animal.

A still further object of the present invention is to provide a head mounted stereotaxic apparatus of the aforementioned type in which the same apparatus can be used on different animal species.

Other objects, advantages, and novel features of the present invention will become apparent from the following detailed description of the invention when considered in conjunction with the accompanying drawings.

BRIEF DESCRIPTION OF THE DRAWINGS

FIG. 7 is an enlarged partial cross sectional view taken along line 7—7 of FIG. 3;

FIG. 8 is a top view of the skeleton of a pig and showing the outline of the frontal sinus and outline of the skin layer which is peeled back to use the present invention; and FIG. 9 is a cross sectional schematic overlay of the profile of the present invention showing the placement thereof with respect to portions of the head of an animal to which it is to be attached.

BEST MODE FOR CARRYING OUT THE INVENTION

Figure 1:
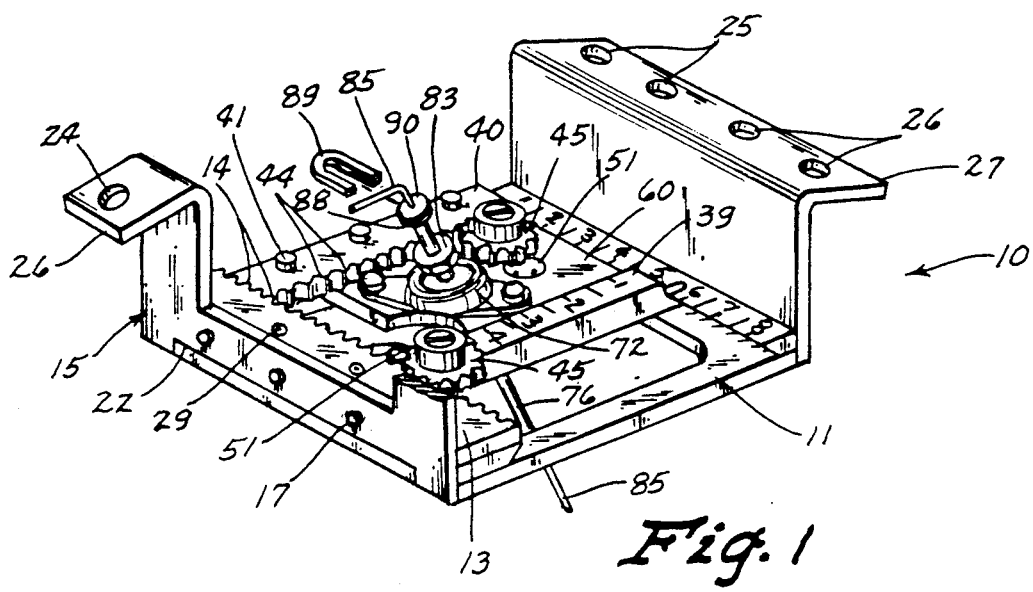
FIG. 1 is a perspective view of a stereotaxic apparatus constructed in accordance with the present invention.

Referring now to the drawings wherein like reference numerals designate identical or corresponding parts throughout the several views, FIG. 1 shows a stereotaxic apparatus (10) constructed in accordance with the present invention. A base member (11) has measuring indicia (12) on one side thereof and a ratchet (13) having teeth (14) thereon. The base member (11) has a pair of mounting brackets (15) and (16) for attachment to each end thereof by threaded fasteners (17) which extend through openings (18) in members (15) and (16). Projections (20) and (21) on the base member (11) fit into grooves (22) and (23) of brackets (15) and

(16) to help prevent movement of the bracket (15) and (16) with respect to the base member (11), to create a more rigid unit.

Openings (24) and (25) in flanges (26) and (27) are provided for attachment by metal screws (93) to the skull of an animal as will be explained below. Threaded fasteners (29) extend through openings (30) in ratchet (13) and are threadably engaged with the base member (11) into threaded openings (31).

A first translating member (35) has beveled edges (36) therein which extend into dovetail grooves (37) and (38) of base member (11) so that the first translating member (35) can move back and forth with respect to the base member (11).

The first translating member (35) has measured indicia (39) on one side thereof and a ratchet bar (40) attached to the other side thereof by threaded fasteners (41) which extend through openings (42) in the ratchet bar (40) and into threaded openings (43) in the first translating member (35). Ratchet bar (40) has teeth (44). A toothed cog gear (45) is rotatably mounted to the first translating member (35) by a pin (46) which extends through an opening (47) in the first translating member (35), through an opening (48) in the toothed cog gear (45) and which pin (46) is held by a set screw (49). This cog wheel structure is substantially identical to the gear cog shown in FIG. 7 which will be explained in detail below. A locking pin (51) is biased by compression spring (52) which is held in opening (53) in the first translating member (35) so that a pointed portion (54) of the pin (51) extends between two of the teeth (55) of the gear cog (45) to prevent the gear cog (45) from rotating with respect to first translating member (35) when end (54) is in such a position, as shown by an identical pin (54) in FIG. 7.

A second translating member (60) has edges (61) thereon that fit into dovetail grooves (62) and (63) of the first translating member (35) for permitting the second translating member (60) to be movable back and forth along a straight line with respect to the first translating member (35). Another gear cog (45) is held to the second translating member (60) by a pin (46) which extends through opening (66) in the second translating member (60). Another set screw (49) holds the gear cog (45) in a fixed relationship with the pin (46) similar to the previous explanation of the gear cog (45) associated with the first translating member (35). A pin (54), as shown in FIG. 7, extends upwardly between the teeth (55) on gear cog (45) by a compression spring (52) pushing upwardly on pin (51). The gear cog (45) will not turn while the pin (54) is in the position shown in FIG. 7, but when the pins (51) and (54) are pushed down, the gear cog (45) can be rotated by insertion of and turning of a screwdriver or the like into a slot (68) in the top of pin (46).

Figure 2:
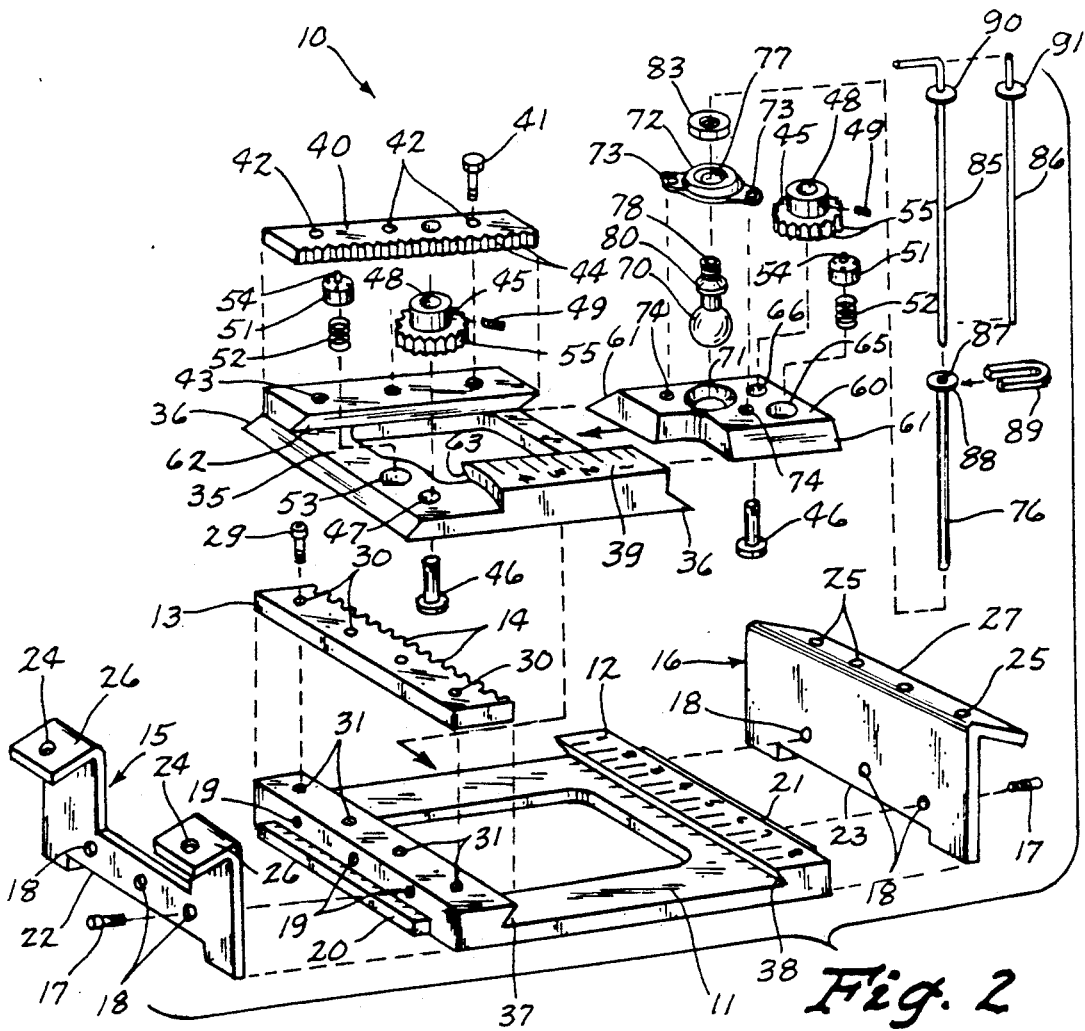
FIG. 2 is a perspective exploded view of the apparatus of FIG. 1.
Figures 5, 6:
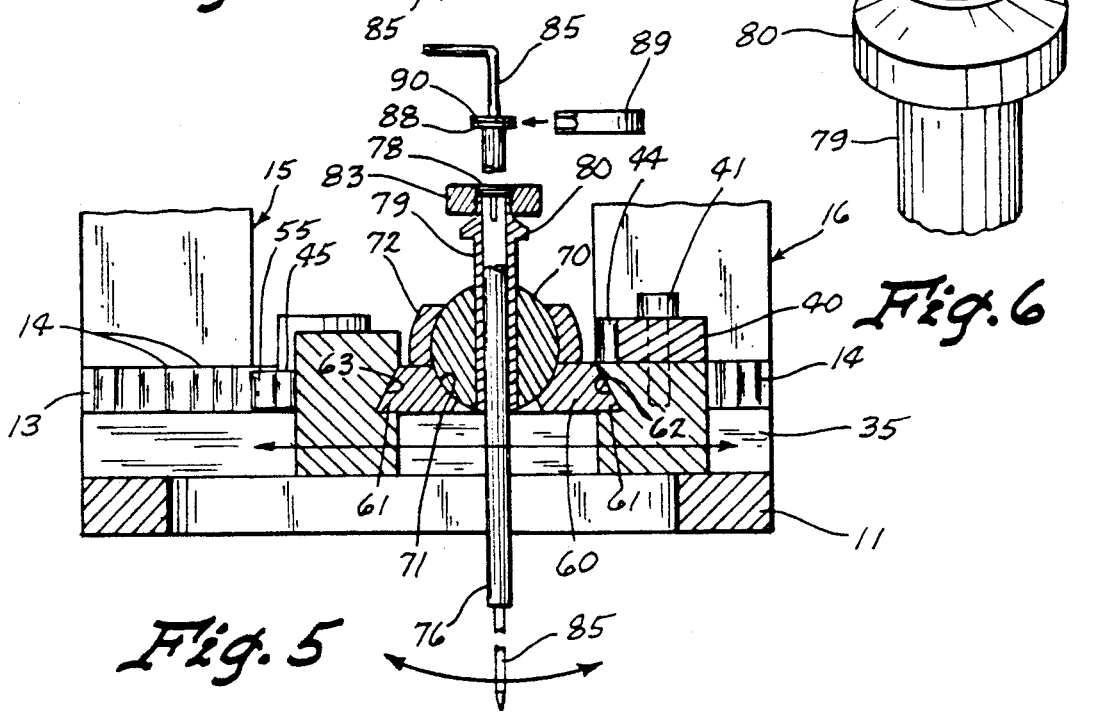
FIG. 5 is a cross sectional view taken along line 5—5 of FIG.. 3.
FIG. 6 is a partial perspective view of the structure which holds the tube for allowing the tube to either slide therein or be locked in a specific position therein.

A universal ball (70) is received into a partially spherical surface (71) in the second translating member (60) and has a clevis (72) which extends down over the spherical portion of the ball (70), as shown in FIGS. 5 and 2 to hold the ball (70) in place. Threaded fasteners (75) extend through openings (73) in the clevis (72) and into threaded openings (74) in the second translating member (60).

A tubular member (76) extends down through the opening (77) in clevis (72) and through the opening (78) in tubular member (79) (FIGS. 5 and 6). An enlarged collar (80) on member (79) supports a threaded portion (81) having four slots (82) disposed therearound. This permits the tube (76) to be easily slid down into the opening (78) and then a threaded nut (83) engages the threads (81) and when this nut (83) is tightened down sufficiently, it will pinch in the top of the grooves (82) so that the inside of the threaded portion (81) engages the outside of the tube (76) to securely hold it in whatever position is desired with respect to the tube (79). It is noted that the tube (79) is rigidly affixed with respect to the swivel ball (70) as is shown in FIG. 5, for example by a set screw (not shown) extending through swivel ball (70).

A probe (85) or (86) can extend down through the opening (87) in the enlarged head (88) of the tube (76) and a U-shaped clip (89) can be used to hold the enlarged head (88) and the enlarged head (90) or (91) securely together to prevent further sliding of the probe (85) with respect to the tube (76). If it is desired to replace the probe (85) by another type of probe (86), the clip (89) is removed, the probe (85) pulled upwardly out of the tube (76), the other type of probe (86) is inserted into the opening (87) in tube (76) and the clip (89) is reinserted over enlarged heads (88) and (91), to hold the probe (86) in whatever position is desired.

In order to use the stereotaxic apparatus (10) shown in FIGS. 1-7, it first must be attached to an animal, such as the pig head shown in FIGS. 8 and 9. FIG. 8 shows an outline of the frontal sinus in dashed lines and an outline of a fat skin layer to be peeled back in order to install the stereotaxic device (10) into the skull (92).

Once the skin layer is cut along the three sides shown in solid lines in FIG. 8, then such skin layer is peeled back, for example, to the right as shown in FIG. 8. Once that is done, the portions of the frontal bone shown in dashed lines in FIG. 9 is removed and a portion of the sinus cavity is also removed to make room for the apparatus (10) as shown schematically in FIG. 9. Once that is done, stainless steel screws (93) are utilized to extend through openings (24) and (25) in flanges (26) and (27) to firmly secure the flanges (26) to the frontal bone which still remains after the dashed portion of the frontal bone is removed.

While only a portion of the apparatus of the stereotaxic apparatus (10) is shown in FIG. 9, it is to be understood that the entire apparatus shown in FIG. 1 is installed in the head of the animal (92). During the process, this will require that one or more holes be bored through the calvarium bone in order to permit the tube (76) to extend into the brain and/or septum of the animal (92).

The head mounted stereotaxic apparatus (10) is designed for precise localization of probes-cannulas inserted into the mammalian brain. The apparatus (10) is fabricated entirely of stainless steel, is non-toxic and can be readily sterilized for aseptic attachment to the head of an animal. Once the apparatus is firmly attached to the frontal bone, as shown in FIG. 9 and the probe/cannula (85) or (86) is set in the proper location in the brain, the skin flap is sutured back in place for a aseptic protection of the bone, sinuses and the dura mater overlying the brain. A plastic tube (95), attached to the top of tube (85), is positioned as shown in FIG. 9 so that it extends out through the animal's skin. The plastic tube (95) then allows substances to be inserted or withdrawn through probe tube (85) as desired without disturbing the sutured skin layer.

The metal probes (85) and (86) can take the form of: (a) cannula for the delivery of drugs, hormones or solvent vehicle to selected sites; (b) cannula for withdrawal of intracerebroventricular fluid; (c) insulated metal probes with exposed tips for recording electrical activity of selected nuclei; (d) insulated metal probes with exposed tips for electrolytic lesion of selected nuclei; (e) push-pull cannula for infusion of drugs, hormones or vehicle and the simultaneous withdrawal of fluids from selected sites for assay of hormones and drugs; and (f) insulated metal probes with exposed tips for recording shifts in potential hydrogen, ions and free radicals in selected nuclei or ventricular regions.

A novel aspect of the present invention is the fact that the apparatus is attached to the animal's head by metal screws to exposed frontal bone. This allows complete mobility of the animal for long-term drugs/hormone delivery/withdrawal, recording or fluid withdrawal from selected regions of the brain. The apparatus (10), fabricated of stainless steel, allows versatility of movement in a horizontal field of 38 mm and a vertical field of 35 mm by ratchet-cog assemblies (13), (45), (40) and (45) with lock pins (51) and (54) to hold the cogs (45) in a selected position. The probe-cannula is inserted in the central shaft of the swivel ball (70) and is held firmly in position by adjusting set screws (75) in the overlying clevis (72). The depth of the probe/cannula is adjustable as explained above, and once the desired depth is achieved, the probe/cannula is locked in place by adjusting a set screw (not shown) on the slotted shaft on the dorsal aspect of the swivel ball (70).

The swivel ball (70) allows for a variety of angles, inclusive of 360°, for probe/cannula placement in the brain to avoid major surface blood vessels of the cerebrum. The overall dimensions of the apparatus (10) (50 mm horizontal and 60 mm vertical) allow its placement just dorsal to the exposed dura mater and attachment by stainless steel screws (93) to the frontal bone (92). The vertical end pieces or brackets (15) and (16) are detachable by three set screws (17) for replacement with different shaped brackets for attachment to the frontal bone of different-shaped heads within a species or for different species of animals. The apparatus (10) can be miniaturized or enlarged to allow it to fit animals either smaller or larger.

Figure 3:
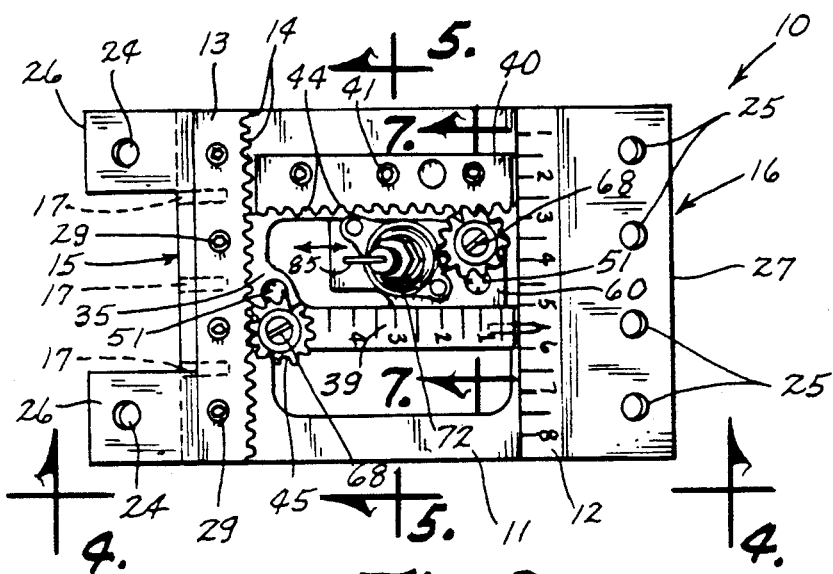
FIG. 3 is a top view of the stereotaxic apparatus of FIG. 1.
Figure 4:
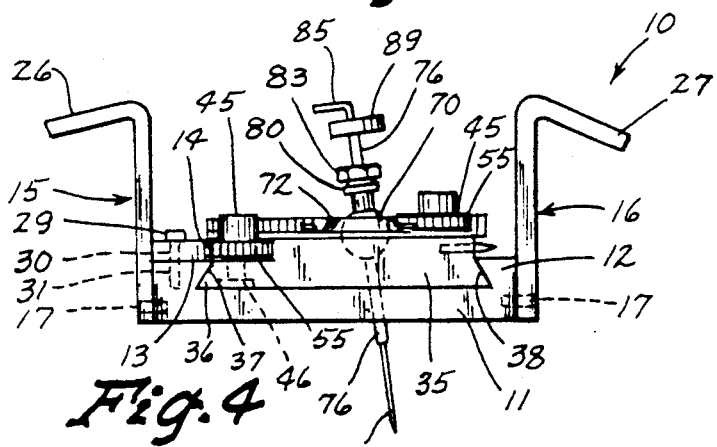
FIG. 4 is a side elevational view taken along line 4—4 of FIG. 3.

Looking to FIG. 3, it is noted that if it is desired to move the probe (85) to the left or right, the upper right cog (45) is utilized by first depressing the pin (51), and then rotating the cog (45) with a screwdriver or the like into slot (68). Rotation of the cog (45) in a clockwise manner will move the probe (85) to the left and rotation of the cog (45) in a counterclockwise direction will move the probe (85) to the right. Indicia (39) on the first translating member (35) can be used to provide half of the coordinates if a coordinate system is desired to be used. Before its insertion into the brain, the probe (85) can be moved in a perpendicular direction, which would appear to be up and down as viewed in FIG. 3. To do this, the lower left gear cog (45) is utilized by first pushing down the locking pin (51), and then using a screwdriver into the slot (68) to move the first and second translating members (35) and (60) together in one direction or the other. Rotation of the lower left cog (45) in a clockwise direction as viewed in FIG. 3 will cause the first and second translating members (35) and (60) and thereby the probe (85) to move down and rotation in a counterclockwise direction will cause the first and second translating members (35) and (60), and thereby the probe (85), to move up as viewed in FIG. 3. Indicia (12) as shown in FIGS. 2 and 3 can also be used as the other part of the coordinate system if so desired.

It will therefore be appreciated from the above description of the apparatus (10) that it can readily be adjusted in two directions perpendicular to each other by using the ratchet cogs. The probe (85) can also be pivoted about 360° by loosening the screws to the clevis (72) and then tightening the screws (75) back down to lock it in place when in a desired position. Additionally, the tube (76), and thereby the probe (85), can be adjusted in or out by loosening or tightening the threaded member (83) shown in FIG. 5.

Accordingly, it will be appreciated that the preferred embodiment disclosed herein does indeed accomplish the aforementioned objects. Obviously many modifications and variations of the present invention are possible in light of the above teachings. It is therefore to be understood that, within the scope of the appended claims, the invention may be practiced otherwise than as specifically described.

We claim:

1. Brain probe positioning apparatus comprising:
    a base member;
    means for selectively attaching said base member to portions of the skull of a living animal;
    a first translating member;
    means for slidably attaching said first translating member to said base member in a first straight line;
    first moving means for selectively moving said first translating member along said first straight line;
    first locking means for selectively locking said first translating member against movement with respect to said base member;
    a second translating member having an opening therethrough;
    means for slidably attaching said second translating member to said first translating member in a second straight line transverse to the first straight line;
    second moving means for selectively moving said second translating member along said second straight line;
    second locking means for selectively locking said second translating member with respect to said first translating member;
    a tube extending through the opening in said second translating member;
    pivotal adjustment means attached to said second translating member for permitting said tube to be universally pivoted 360° about a point; and
    means for locking said pivotal adjustment means in a desired position whereby said tube will be held in said desired position with respect to said second translating member.

2. The brain probe positioning apparatus of claim 1 including:
    means for slidably adjustably the position of said tube with respect to said second translating member; and
    means for selectively locking said tube in a desired position with respect to said second translating member.

3. The brain probe positioning apparatus of claim 1 wherein said first moving means comprises a toothed ratchet rigidly attached to one of the base member and the first translating member and a mating gear cog, having teeth, rotatably attached to the other of said base member and first translating member whereby rotation of said gear cog causes the first translating member to move with respect to said base plate.

4. The brain probe positioning apparatus of claim 3 wherein said gear cog is attached to said first translating member and said first locking means comprises a pin biased to a first position between two of the teeth of said gear cog to prevent rotation of said gear cog, said pin being movable to a second position to allow said gear cog to rotate and thereby said first translating member to move with respect to said base member.

5. The brain probe positioning apparatus of claim 1 wherein said second moving means comprises a ratchet rigidly attached to one of the first translating member and the second translating member and a mating gear cog, having teeth, rotatably attached to the other of said first translating member and said second translating member whereby rotation of said gear cog causes the second translating member to move with respect to said first translating member.

6. The brain probe positioning apparatus of claim 5 wherein said gear cog is attached to said second translating member and said second locking means comprises a pin biased to a first position between two of the teeth of said gear cog to prevent rotation of said gear cog, said pin being movable to a second position to allow said gear cog to rotate and thereby said second translating member to move with respect to said first translating member.

* * * * *